(12) United States Patent
Polak et al.

(10) Patent No.: US 7,956,761 B2
(45) Date of Patent: Jun. 7, 2011

(54) INFRARED GAS DETECTION AND SPECTRAL ANALYSIS METHOD

(75) Inventors: Mark Leon Polak, Redondo Beach, CA (US); Carlton Douglas Nealy, Redondo Beach, CA (US); John P. Stafsudd, Los Angeles, CA (US)

(73) Assignee: The Aerospace Corporation, El Segundo, CA (US)

( * ) Notice: Subject to any disclaimer, the term of this patent is extended or adjusted under 35 U.S.C. 154(b) by 1043 days.

(21) Appl. No.: 11/807,515

(22) Filed: May 29, 2007

(65) Prior Publication Data

US 2010/0090845 A1 Apr. 15, 2010

(51) Int. Cl.
*G08B 17/10* (2006.01)
(52) U.S. Cl. .................. 340/632; 73/23.35; 356/300
(58) Field of Classification Search .............. 340/632; 250/339.09, 339.11, 339.13, 341.5, 252.1; 356/307, 308, 433, 437, 300; 702/23, 24, 702/27–30, 85–87, 189, 190; 73/23.35
See application file for complete search history.

(56) References Cited

U.S. PATENT DOCUMENTS

| 6,341,257 | B1 * | 1/2002 | Haaland ..................... 702/27 |
| 6,396,056 | B1 * | 5/2002 | Lord et al. ................. 250/252.1 |
| 6,580,510 | B2 * | 6/2003 | Nawracala .................. 356/451 |
| 6,629,041 | B1 * | 9/2003 | Marbach ..................... 702/30 |
| 6,653,971 | B1 * | 11/2003 | Guice et al. ................ 342/54 |
| 2002/0158212 | A1 * | 10/2002 | French et al. ............. 250/459.1 |
| 2004/0082070 | A1 * | 4/2004 | Jones et al. ................ 436/8 |
| 2006/0023948 | A1 * | 2/2006 | Palmadesso et al. ....... 382/191 |

* cited by examiner

*Primary Examiner* — Daniel Wu
*Assistant Examiner* — Frederick Ott
(74) *Attorney, Agent, or Firm* — K & L Gates LLP

(57) ABSTRACT

A gas detection system and method for analysis of infrared gas spectra is used for chemical threat detection, quantification and alarm, using a chemical library, a chemical threat list, and a background model that incorporates the data history, allows spectra containing interferent signals into the background model, the model being updated using delay buffering to prevent threat spectra incorporation and using exponential decays to preferentially represent recent background history, all computed in the logarithmic space for rapid detection and alarm.

20 Claims, 2 Drawing Sheets

SPECTRUM ANALYSIS PROCESS

SPECTRUM ANALYSIS PROCESS

INFRARED GAS DETECTION AND SPECTRAL ANALYSIS METHOD

STATEMENT OF GOVERNMENT INTEREST

The invention was made with Government support under contract No. FA8802-04-C-0001 by the Department of the Air Force. The Government has certain rights in the invention.

FIELD OF THE INVENTION

The invention relates to the field of infrared spectroscopy. More particularly, the present invention relates to infrared spectroscopic gas detection.

BACKGROUND OF THE INVENTION

Infrared spectroscopy is a relatively rapid, sensitive, and chemically specific technique for the detection of a large variety of chemicals. However, there are difficulties associated with implementing the technology in a continuous gas detection monitor system requiring a very low false alarm rate and high sensitivity.

Infrared spectroscopy is a well-known technique for chemical identification and quantification. The observed infrared signal I is linked to chemical concentration by Beer's Law equation $I(v)=I_o(v)e^{-\epsilon(v)cl}$, where $I_o$ is the background signal, $\epsilon$ is the absorption coefficient for the chemical of interest, c is the chemical concentration, and l is the path length over which the chemical is observed. I, $I_o$, and $\epsilon$ are all functions of the light frequency v. Concentration is determined by solving a concentration equation $c=-\log[I(v)/I_o(v)]/\epsilon(v)l$.

A critical variable in the concentration equation is the infrared spectrum of the background $I_o(v)$, which is usually measured empirically. This variable quantifies the infrared source that is being passed through the sample of interest. When obtained empirically, the infrared spectrum of the background may also account for detector responsivity and atmospheric constituents in the infrared path that occur both with and without the sample. When making infrared measurements, the background spectrum must be updated frequently to correct for environmental and instrument changes over time. The background spectrum is usually obtained in a clean environment before a sample of interest is introduced to the system. To increase signal-to-noise, the background spectrum may be averaged over an extended period of time.

When infrared spectroscopy is used in a continuously monitoring point sensor, the sample interrogated by the point sensor may be contaminated at any time, and contamination could be due to threat chemicals or interferent chemicals. Threat chemicals are defined as those chemicals that require a user response, while interferent chemicals are all other chemicals. If historical spectra are to be used as a chemical background, the process that chooses these historical spectra must be automated, and the algorithm must somehow determine whether a candidate background spectrum is contaminated. Furthermore, a contaminant may be present over an extended period of time making it impossible to use an empirical spectrum that reflects the current state of the sensor.

An alternative approach is to periodically inject a clean air sample into the continuous monitor. However, clean air injection reduces the duty cycle of the system and requires accurate modeling of atmospheric constituents to accomplish background removal.

The prior art in another area, hyperspectral imaging, suggests an approach for modeling the spectral background. Hyperspectral imaging involves taking an optical image of a location of interest, where each pixel in the image contains a spectrum. When performed in the infrared, chemicals in the scene can be identified by extraction of chemical signatures from the spectra and comparison to library infrared spectra. The background problem for hyperspectral imaging is even more complicated than the simple infrared spectroscopy case. Each pixel in the image, which can contain sky, buildings, or geological features has unique spectral characteristics. A useful technique in hyperspectral imaging, referred to as the matched filter, is to treat the variation in the backgrounds as system noise and model the backgrounds using a mean spectrum and a covariance matrix. The mean vector and the covariance matrix are computed by using all of the spatial elements of the hyperspectral image. Standard least squares techniques can then be used to identify and quantify the chemical signatures present in the hyperspectral image.

Existing infrared spectroscopy systems and methods disadvantageously process threat spectra and interferent spectra identically and different than background spectra. These systems and methods have disadvantageously used static non-decaying backgrounds for threat detection. In hyperspectral imaging, the covariance and mean of the background model has been processed in the linear space, which would be disadvantageous for the continuous monitoring case because of the computational burden. The prior continuous monitoring systems and methods have insufficiently low false alarm rate and insufficiently high sensitivities for many applications. These and other disadvantages are solved or reduced by the present invention.

SUMMARY OF THE INVENTION

An object of the invention is to provide a method for providing gas detection.

Another object of the invention is to provide a method for providing gas detection using spectral data.

Yet another object of the invention is to provide a method for providing gas detection using infrared spectral data in logarithmic space.

Still another object of the invention is to provide a method for providing gas detection using infrared spectral data and an updated chemical background, which is subjected to exponential decay.

A further object of the invention is to provide a method for providing gas detection using infrared spectral data, an updated background model, a threat chemical list, and a spectral library.

Another object of the invention is to provide a method for providing gas detection that models background and interferent-containing spectra as noise.

The invention is directed to an infrared gas detection system and method that detects threat chemicals using a background model based on recent data history. Infrared gas spectra are converted into the log space and are screened for threat chemicals and interferent chemicals. The method is used to determine when one or more of a list of threat chemicals is detected with confidence, to report the concentration, and to trigger alarms. When a threat is detected, alarms are issued. When no threat chemical is detected, the detected spectrum is treated as noise even though the spectrum data may contain signals from interferent chemicals. The spectrum data is added to the background, and hence, to a background model that may then contain interferent signals. Use of this background model will then suppress interferents and achieve enhanced threat chemical detection.

A threat chemical list is a subset of a much larger spectral library, with the remainder of the spectral library regarded as potential interferents. The background spectrum is treated as system noise that is modeled by a mean vector and a covariance matrix. The invention adapts the matched filter techniques typically used in hyperspectral imaging, for modeling the background spectrum $I_o(v)$. A stepwise weighted regression algorithm is used to determine the most likely chemicals in the least squares fit, and returns chemical identities, concentrations, and confidences. When a spectrum is determined not to contain a chemical from the threat list, the spectrum is used to update the background model, after passing through a time-delay buffer, and after application of an exponential weighting procedure that more heavily weights most recent spectra. Interferent spectra allowed into the background model suppress detection of the interferents, but greatly enhance sensitivity to the target threat chemicals. The confidences are t-statistics resulting from a least-squares process used to determine whether an alarm should be sounded.

The method advantageously processes interferent spectra and background spectra as background noise for enhanced threat spectra detection. The infrared spectroscopy method also advantageously processes threat spectra, interferent spectra, and background spectra in a logarithmic space, linearizing the underlying algebra and consequently offering fast processing. The infrared spectroscopy method further advantageously exponentially decays the background model for improved weighted sensitivity to threat detection. These and other advantages will become more apparent from the following detailed description of the preferred embodiment.

DETAILED DESCRIPTION OF THE PREFERRED EMBODIMENT

Figure 1:
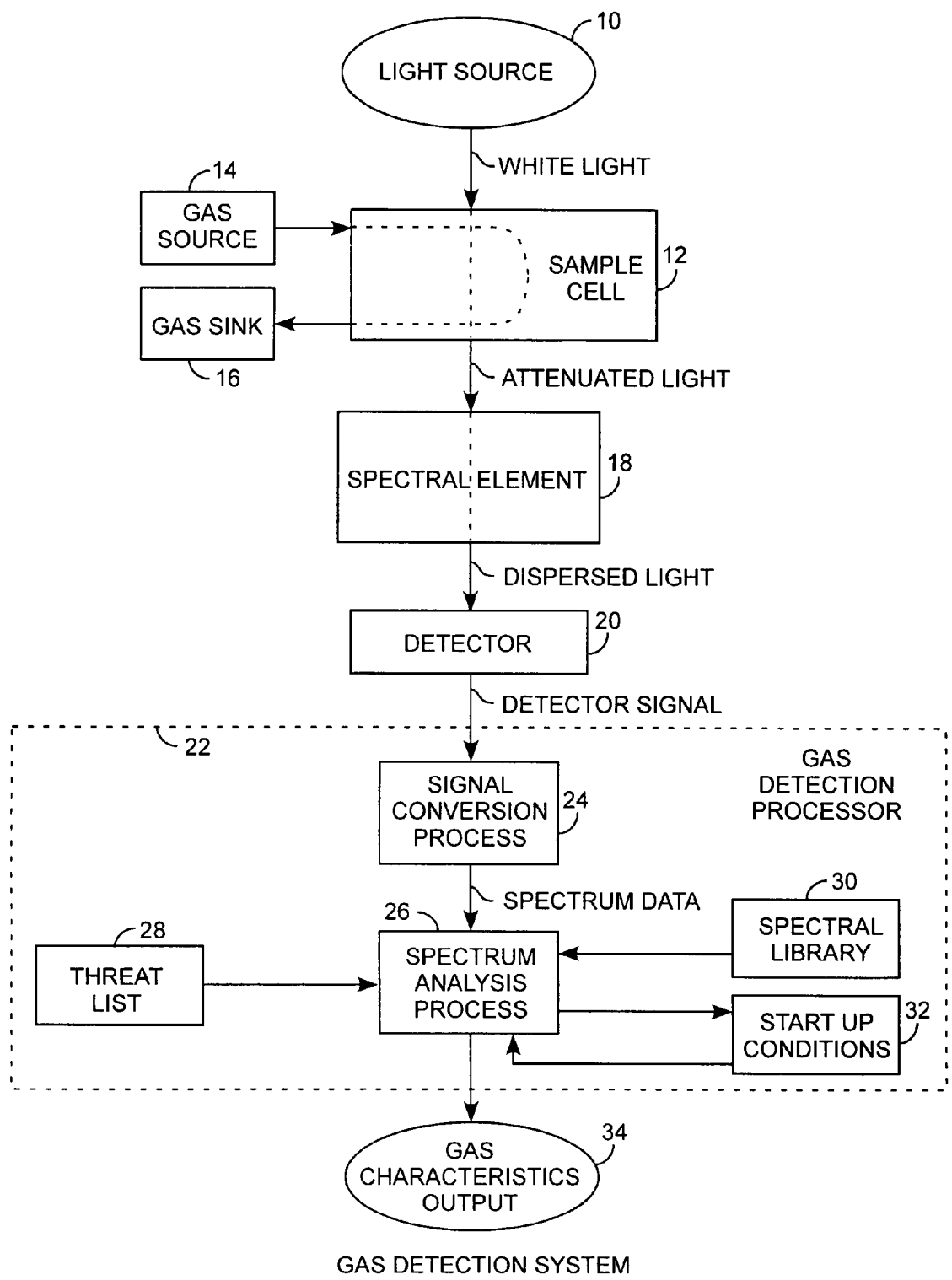
FIG. 1 is a block diagram of a gas detection system.

An embodiment of the invention is described with reference to the figures using reference designations as shown in the figures. Referring to FIG. 1, a gas detection system includes a light source 10 providing white light to a sample cell 12 containing a gas sample from a gas source 14. The gas sample is sourced from the gas source 14, passed through the sample cell 14, and sunk into a gas sink 16. The gas sample attenuates the white light into attenuated light. The attenuated light is passed through a spectral element 18 for translating the attenuated light into dispersed light. The dispersed light is detected by a detector 20 for providing a detector signal to a gas detection processor 22. The gas detection processor 22 converts the detector signal into spectrum data using a signal conversion process 24. The gas detection processor 22 then uses a spectrum analysis process 26 to receive the spectrum data, a spectral library 30, start up conditions 32 of a chemical background, and a chemical threat list 28. The spectrum analysis process then provides a gas characteristics output that includes gas identifications (IDs), alarms, and concentrations. The light source 10, sample cell 12, spectral element 18, and detector 20 are conventional components. However, the gas detection processor 22 is improved to implement the gas detection method.

The light source 10 provides the white light that is passed through a constantly changing sample and is separated into spectral components by some dispersion means 18. The spectrally separated dispersed light impinges on the detector 20 for providing an infrared detector signal. The signal conversion process 24 may be a conventional signal processing method for converting the infrared detector signal into infrared spectrum data. The method uses this infrared spectrum data to identify and quantify chemical constituents in the sample and to deliver confidence metrics in the form of t-statistics for the gas detection. The method uses these confidence metrics to make alarm decisions.

Figure 2:
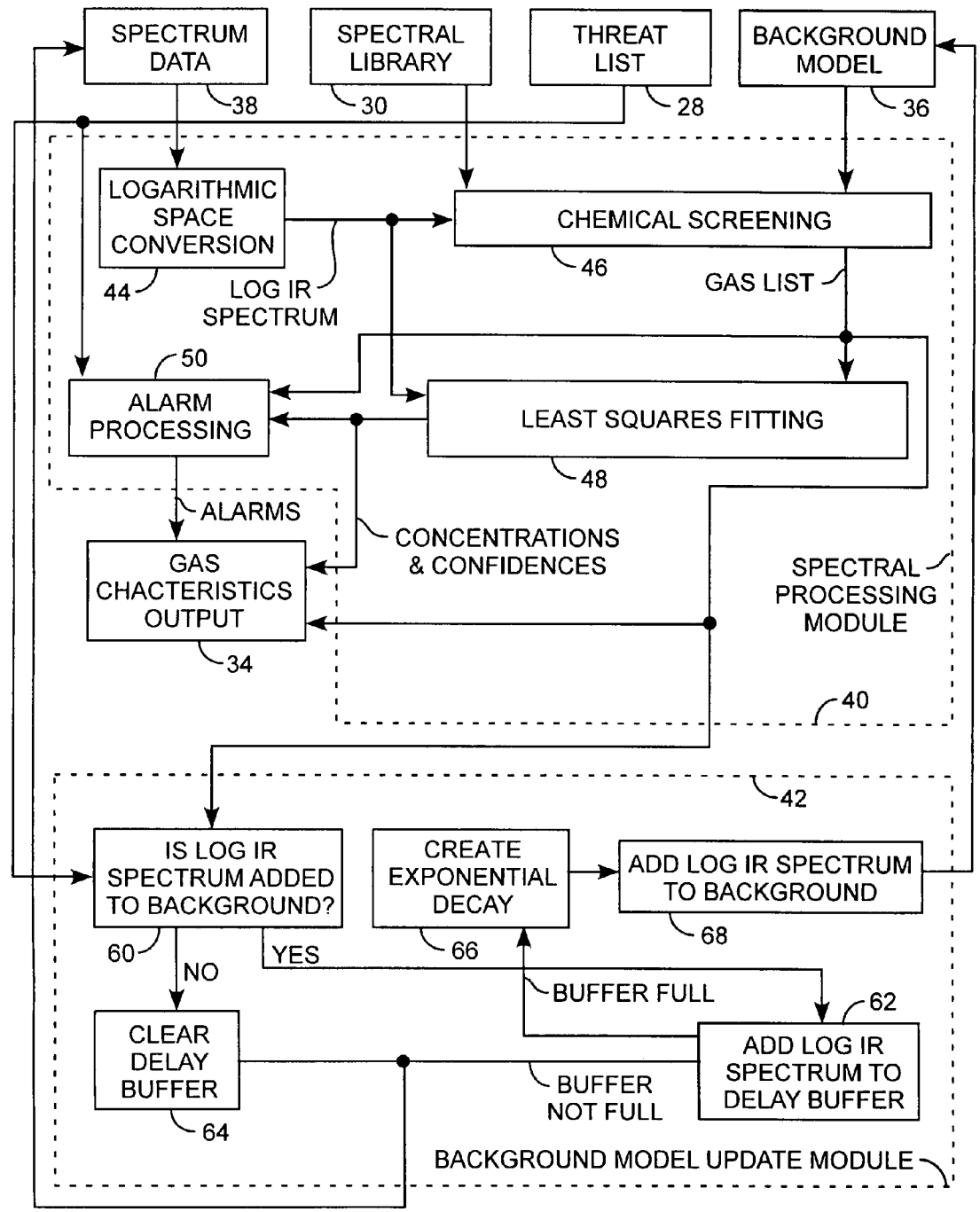
FIG. 2 is flow chart of a spectrum analysis process.

Referring to FIGS. 1 and 2, and more particularly to FIG. 2, the spectrum analysis process includes a spectral processing module 40 and a background model update module 42. The spectral processing module 40 requires a spectral library 30 and a threat list 28. The initial start conditions 32 include an initial background model 36. The spectral processing module 40 analyzes the spectrum data of the gas sample to identify interferents and threat chemicals contained in the gas library 30. The background model update module 42 repetitively updates the background model with new spectrum data so as to model the changing background. The background model update module 42 does not allow spectrum data containing threat chemical signals into the background module 36. However, the background model update module 42 does allow spectrum data containing interferent signals to enter the background model 36.

The spectrum data is an infrared spectrum, which is the result of passing radiation through the gas sample of interest. At each light frequency, the infrared spectrum is treated to be linearly related to the power incident on the spectrometer detector. Arrival of an infrared spectrum triggers execution of the spectral processing module. The infrared spectrum is described as a vector, z, with each vector component corresponding to a light frequency. The spectrum vector z has m frequency components.

The spectral library 30 is a collection of laboratory infrared spectra for all chemicals, which might be present in the environment including benign interferents and threat chemicals. The infrared spectra are specified as absorbance as a function of light frequency for each chemical. The spectra must correspond to a designated column density of chemical in units such as ppm-m or $g/m^2$, when the method is used quantitatively. Each database spectrum is a spectrum vector k.

The threat list 28 is a list of threat chemicals found in the spectral library 30. The threat chemical list is a list of chemical names that correspond to a subset of the spectral library 30. These threat chemicals are those that will trigger alarms when present. The spectrum analysis process treats the threat chemical list differently from the remainder of the interferent chemicals in the spectral library 30.

The background model 36 is initially set to the start up conditions 32, defined by a start up mean vector and a start up covariance matrix. The startup mean vector and the start up covariance matrix include a collection of N spectra taken by the system. The mean vector elements are determined by a mean vector equation $$\mu_i = \sum_{k=1}^{N} (Y_i(k))/N$$

and covariance matrix equation $$S_{ij} = \sum_{k=1}^{N} (y_i(k) - \mu_i)(y_j(k) - \mu_k)/(N-1),$$

where $\mu$ is the mean vector, $S_{i,j}$ are the elements of the covariance matrix S, where $y=\log(z)$, and $y_i(k)$ is the i-th frequency element of the log of the k-th infrared spectrum. The spectral processing module requires a start up mean vector and start up covariance matrix as the start up conditions. The start up conditions can be generated with a collection of spectra taken in a clean environment with the number of spectra being greater than the number of light frequencies m to avoid singularity. The background model 36 is typically initialized with spectrum data generated from sampling by the system without a threat chemical in the sample cell 12. The start up conditions 32 can alternatively be stored values from a previous run of the background model update module 42. A normalization constant c that tracks the number of spectra used to construct $\mu$ and S, is also tracked and would equal N. The background model 36 when updated provides a current mean vector and a current covariance matrix. The mean vector and the covariance matrix of the background model 36 are used by the spectral processing module 40, along with a normalization constant c.

A logarithmic space conversion 44 converts the spectrum data into the log space. Converting the infrared spectrum z to log space with $y=\log(z)$ creates a linear relationship between the observed signal of the spectral data and the species concentrations. Processing of spectral data in the log space conserves computational resources. The log space conversion 44 provides the log of the infrared spectrum of the spectrum data as a vector y of m components.

A chemical screening 46 process is used to identify chemicals that contribute to the infrared spectrum of the spectrum data. The screening process consists of conventional stepwise least square linear regression. The chemical screening process 46 receives the log infrared spectrum and determines gases from the spectral library 30 of gases that are present in the spectrum data. The chemical screening process 46 steps through the entire spectral library 30 fitting the spectrum data using one specific chemical at a time as initial least square fitting. The spectrum data is modeled by a spectrum equation $y=X\beta+v$, where X is an m×2 matrix with a first column containing the library spectrum k and a second column containing the mean vector. The term $\beta$ is a 2×1 vector consisting of a chemical concentration factor as a first element, and a scalar as a second element that scales the background mean. The m×1 vector v models background clutter plus noise. The vector v is characterized by a m×m matrix $\sigma^2 S$, where S is the covariance matrix and $\sigma$ is a scaling parameter, which is returned during fitting. For each of the specific chemical screening steps, the screening process generates a concentration and confidence metric referred to as a t-statistic.

The chemical screening process 46 uses least squares fitting to determine the likelihood of a chemical presence by generating a confidence metric t-statistic. The weighted least squares estimate of the parameter $\beta$ is given by a $\beta$ equation $\beta=(X^T S^{-1} X)^{-1} X^T S^{-1} y$. An accuracy equation $\Sigma=\sigma^2(X^T S^{-1} X)^{-1}$ provides the matrix $\Sigma$ that characterizes the accuracy of the estimated parameter vector $\beta$, where $\sigma^2=\Sigma(y-X\beta)^T S^{-1}(y-X\beta)/(m-2)$. The estimated concentration of the chemical of interest is the first element of $\beta$ is denoted $\beta_1$. The variance of the estimated concentration is the matrix element $\Sigma_{1,1}$. The confidence t-statistic is used by the spectral processing module as a confidence metric. The confidence t-statistic is given by a t-statistic equation $t=\beta_1/\sqrt{\Sigma_{1,1}}$.

After stepping through the entire gas library 30, the detected chemical with the highest confidence t-statistic is retained, and is designated the retained chemical. When the confidence t-statistic for the retained chemical is below a user-defined confidence t-statistic, the procedure is halted, and the final least squares fit is performed with just the single retained chemical for subsequent adding to the background model 36. When the confidence t-statistic for the retained chemical is above a user-defined confidence t-statistic, the chemical screening process 46 is repeated through the library 30. The retained chemical is retained on the gas list. The matrix X is an m×3 matrix, where the first column is the library spectrum of the retained chemical, the second column is the spectrum of the chemical being tested, while stepping through the library, and the third column represents the mean vector. At the conclusion of stepping through the library 30, the chemical with the highest confidence t-statistic is identified and retained on the gas list for future fits. If the confidence t-statistic is below the user-defined threshold, the procedure is halted.

This screening process 46 is repeated until either the t-statistic of the most recently retained chemical is below threshold, or a user-defined maximum number of chemicals are chosen. Upon termination of the chemical screening process, a gas list of detected chemicals, which are the chemicals retained by the chemical screening process, is passed to the final least square fitting process.

The final least square fitting process 48 is limited to only the detected chemicals on the gas list, and recomputes the confidences and concentrations. This final least squares fitting process 48 recomputes the concentrations and confidences of retained chemicals on the gas list generated during the screening process. This recomputation is optional for purposes of code minimization by merely keeping track of only the gas list. The final least squares calculations are applied using the X matrix that includes only the detected chemicals. The final least square fit provides the recomputed concentrations and confidences indexed to the list of detected chemicals, including detected interferents and threats.

Alarm processing 50 receives the gas list from the chemical screening process and receives the concentrations, and confidences from the final least square fitting. This alarm process 50 examines the threat list, gas list, concentrations, and confidences and determines when an alarm is mandated. An alarm is mandated when the detected chemical is a threat chemical, when a user-specified concentration for that chemical is exceeded, and when a user-specified confidence t-statistic is exceeded. The user-specified concentration can be set to zero.

The spectral processing module 40 provides the gas characteristics output 34 including the gas list of detected chemicals, to the background model update module. The log infrared spectrum from the log conversion is also available for background model updating.

The first step 60 of the background model update module determines if the log IR spectrum should be added to background. A decision is made based on the presence of threat chemicals in the gas list. If chemicals in the gas list are on the threat list, the current log IR spectrum is not incorporated into the background model 36. When no detected chemicals are on the threat list, the log IR spectrum is allowed into the background model 36. The log IR spectrum that is allowed into the background model may contain interferents, but will not include any threat chemicals.

Adding 62 of the log IR spectrum to the delay buffer occurs when the gas list does not contain a threat chemical. When a spectrum is selected for incorporation into the background model 36, the log IR spectrum is passed into a delay buffer of user-specified size. The delay buffer does not pass the log IR spectrum out until it is filled, whereupon the buffer will deliver the oldest log IR spectrum and the process will proceed to the create exponential decay step. If the delay buffer is not filled, the background model update module will terminate, and the spectrum analysis process 26 will await more spectrum data.

A clear delay buffer step 64 occurs when the gas list contains a threat chemical. In this case, the entire delay buffer is cleared, and the buffer will not deliver a log IR spectrum until it is filled again. The purpose of clearing the delay buffer is that the detection of a threat chemical indicates a high likelihood of lower levels of threat chemicals in the recent spectrum history. The delay buffer is cleared to prevent these spectra from contaminating the background.

The exponential decaying 66 of the current mean and covariance matrix ensures that the background model preferentially reflects the recent background history. An exponential decay factor is applied to the mean vector and covariance matrix. The mean and covariance are multiplied by the exponential decay factor before adding new data. Because this multiplication is performed on each iteration of the background model update module 36, the exponential factor is used to bias the mean and covariance to reflect recent data more strongly than older data. In this step the decay factor r is determined by a decay factor equation $r=\exp(-1/T_c)$, where $T_c$ is the desired 1/e decay period measured in number of spectra. The exponential decay of the covariance and mean is performed before adding in a new spectrum. As such, the background model will weigh recent data more heavily than older data. If data were simply added to the covariance and the mean with the collection of each spectrum, the effect of recent data would eventually become very small compared to the large volumes of accumulated data. To prevent this occurrence, the mean and covariance are weighted by an exponential decay factor before adding new data to the background model 36.

Adding the Log IR spectrum 68 to the background models requires the computation of an updated mean and covariance matrix. In adding the log IR spectrum, the infrared spectrum delivered by the time delay buffer is added to the background model, employing the exponential decay factor r. A new normalization factor c' is computed from the old normalization factor c by a normalization factor equation $c'=1+rc$. The normalization factor reflects the number of spectra, which have contributed to the mean vector and covariance matrix. The new mean vector $\mu'$ is calculated using the old mean vector $\mu$ and the infrared spectrum y using a mean equation $\mu'=\mu+(y-\mu)/c'$. The elements of the new covariance matrix S' are given by covariance equation $S_{ij}=\{(y_i-\mu_i')(y_j-\mu_j')+crS_{ij}+cr(\mu_i'-\mu_i)(\mu_j'\mu_j)\}/c'$. The new covariance matrix S', mean vector $\mu'$, and normalization constant c' are passed to the spectral processing module. After updating the background model, the updated background model is then used during subsequent chemical screening. As such, interferent containing spectra are continuously being adding to the background model 36 for the detection of threat chemicals.

The purpose of the background model update module 42 is to provide the spectral processing module with a new mean and covariance matrix for modeling the background in the least squares calculation. The method employs log space conversions for linearizing the underlying data for fast execution of the method, allows interferent spectra into the background model for enhanced detection of threat chemicals, delays background updates for keeping threat chemical spectra out of the background model 36, and decays the background for preferential representation of recent history in the background model. Significantly, the method treats differently threat chemical detection and interferent chemical detection by treating interferent spectra as noise in the background model. The method operates in the logarithmic space and updates the background mean and covariance. Updating the background mean and covariance includes the prevention of spectra containing threat chemicals from entering the background model, allowance of spectra containing interferent chemicals into the background, the use of a time delay buffer, and exponential decay of the covariance and mean to more heavily weight recent background history. Instead of making a selection, the method treats the current background as a linear combination of previously observed backgrounds, and the linear least squares processing is used to optimize the background model.

The method applies matched-filter techniques to the active infrared point sensor gas detection system. Whereas hyperspectral imaging obtains its background model by using diverse spectra in the spatial domain, the method uses diverse spectra from the background history in the time domain to model the background. The method applies the matched filter technique to the active-infrared spectrum. The matched-filter technique is adapted to the active-infrared sensor using Beer's Law. With multiple chemicals, the infrared spectrum in Beer's Law equation can be expressed as the interferent log equation $\text{Log } I=(\log I_0\Sigma_{interferents}\epsilon_i c_i\lambda+\text{noise})-\Sigma_{target-chemicals}\epsilon_i c_i l$, where $\log I_0$ is the log of the background spectrum ($I_0$), $\Sigma_{interferents}\epsilon_i c_i l$ is the spectral contribution of the interferents, noise represents instrument noise, and $\Sigma_{target-chemicals}\epsilon_i c_i \lambda$ represent the spectral contribution of the target chemicals. The terms in parentheses will be modeled as system noise through the use of a mean vector and covariance matrix, both of which are built up using the logarithms of historical spectra.

The invention is directed to a system and method for threat chemical detection by receiving an infrared spectrum and determining when threat chemicals are present. The method provides gas IDs, gas concentrations, detection confidence, and an alarm decision. The method relies upon continuously monitoring active IR spectroscopy, where active IR means using an artificial light source, with continuously changing samples. The system can be used in a point sensor for taking in air from a single location, or fence-line monitoring with a light source that is down an open-path from a detector. The method can be operated continuously without human intervention, and does not require independent calibration. The primary application of interest is use of the method is in infrared point detectors, which continuously protect a site. Such point detectors could be used to protect high-value sites from chemical attack, or used in industrial settings to protect personnel against accidental exposure. The method can be used to monitor buildings, subways, and other public facilities. The method provides for sensitive detection with reduced false alarms. Those skilled in the art can make enhancements, improvements, and modifications to the invention, and these enhancements, improvements, and modifications may nonetheless fall within the spirit and scope of the following claims.

What is claimed is:

1. A method for detecting a threat being a threat chemical in an illuminated gas sample containing an interferent being an interferent chemical, the threat being in a threat list, interferent and threat being listed in a library of spectra of threats and interferents, method comprising the steps of, receiving, by a gas detector processor from a detector, a detector signal, the detector signal being a spectrum of the illuminated gas sample, generating, by the gas detector processor, a background, the background defined by a mean and a covariance, converting, by the gas detector processor, the detector signal into spectrum data, screening, by the gas detector processor, the spectrum data for a detected chemical, wherein screening the spectrum data comprises screening the spectrum data using the mean and covariance of the background, adding, by the gas detector processor, the spectrum data to the background when the detected chemical is not a threat, and wherein the spectrum data is old spectrum data, the method further comprising the steps of, delaying the adding of the old spectrum data to the background, repeating the receiving, converting, and screening steps for generating new spectrum data, the screening step indicating the new spectrum data is a threat, and skipping the adding step.

2. The method of claim 1 wherein, the detector signal is an initial spectrum, the background in the generating step is an initial background, and the background in the adding step is an updated background.

3. The method of claim 1 wherein, the background in the generating step is a current background, the background in the adding step is an updated background, the method is repeated for a plurality of the illuminated gas samples, and the updated background becomes the current background after each execution of the method.

4. The method of claim 1 further comprising the step of, converting, by the gas detector processor, the spectrum data into log data, the screening and adding steps are executed in log space.

5. The method of claim 1 further comprising the step of, exponentially decaying the background prior to adding the spectrum data, wherein recent spectrum data is weighted heavier than prior spectrum data.

6. The method of claim 1 wherein, the screening step uses stepwise least square regression process to detect the threat.

7. The method of claim 1 wherein, the screening step uses stepwise least square regression process to detect the interferent.

8. The method of claim 1 further comprising the step of, alarming when the threat is detected.

9. The method of claim 1 wherein, the spectrum data is infrared spectrum data.

10. The method of claim 1 wherein, the screening step generates concentrations and confidences for detected threats and interferents.

11. The method of claim 1 wherein, the screening step generates concentrations and confidences for detected threats and interferents, the detected threats are retained on a gas list as retained chemicals.

12. The method of claim 1 wherein, the screening step generates concentrations and confidences for detected threats and interferents, a detected chemical with the highest confidence is an interferent having an interferent spectrum that is added during the adding step to the background.

13. A method for detecting a threat being a threat chemical in an illuminated gas sample containing an interferent being an interferent chemical, the threat being in a threat list, interferent and threat being listed in a library of spectra of threats and interferents, method comprising the steps of, receiving, by a gas detector processor from a detector, a detector signal, the detector signal being spectra of the illuminated gas sample, generating, by the gas detector processor, a background, the background defined by a mean and a covariance, converting, by the gas detector processor, the detector signal into spectrum data, converting, by the gas detector processor, the spectrum data into an IR log spectrum, screening, by the gas detector processor, the IR log spectrum for detected chemicals using the mean and covariance of the background, the background model defining interferent spectra, adding, by the gas detector processor, the IR log spectrum to the background when no threat is detected, regardless of whether an interferent is detected in the IR log spectrum, exponentially decaying, by the gas detector processor, the background prior to adding the IR log spectrum.

14. The method of claim 13 wherein, the method is repeated, the decaying step serves to weight recent IR log spectrum more heavily than prior IR log spectrum.

15. The method of claim 13 further comprising the step of, alarming when the threat is detected.

16. A method for detecting a threat being a threat chemical in illuminated gas sampled containing an interferent being an interferent chemical, the threat being in a threat list, interferent and threat being listed in a library of spectra of threats and interferents, the method comprising the steps of, receiving, by a gas detector processor from a detector, a first detector signal, the first detector signal being a spectrum of a first illuminated gas sample, generating, by the gas detector processor, a background, the background defined by a mean and a covariance, converting, by the gas detector processor, the first detector signal into first spectrum data, screening, by the gas detector processor, the first spectrum data for a detected chemical, holding, by the gas detector processor, the first spectrum data in a buffer when the detected chemical is not a threat, the buffer having a size for storing N spectra, wherein $N \geq 1$, repeating, by the gas detector processor, the receiving, converting, and screening steps using N subsequent spectrum data from N subsequent detector signals for N subsequent illuminated gas samples, and adding, by the gas detector processor, the first spectrum data held in the buffer to the background when screening of the N subsequent spectrum data for the N subsequent illuminated gas samples detects no threats.

17. The method of claim 16, further comprising applying an exponential decay factor to the mean and covariance of the background prior to adding the first spectrum data held in the buffer to the background such that recent spectrum data is weighted heavier than older spectrum data.

18. A method for detecting a threat being a threat chemical in an illuminated gas sample containing an interferent being an interferent chemical, the threat being in a threat list, interferent and threat being listed in a library of spectra of threats and interferents, method comprising the steps of, receiving, by a gas detector processor from a detector, a detector signal, the detector signal being spectra of the illuminated gas sample, generating, by the gas detector processor, a background, the background defined by a mean and a covariance, converting, by the gas detector processor, the detector signal into spectrum data, converting, by the gas detector processor, the spectrum data into an IR log spectrum, screening, by the gas detector processor, the IR log spectrum for detected chemicals, the background model defining interferent spectra, the IR log spectrum indicating an interferent and a threat, adding, by the gas detector processor, the IR log spectrum to the background when no threat is detected, regardless of whether an interferent is detected in the IR log spectrum, exponentially decaying, by the gas detector processor, the background prior to adding the IR log spectrum, wherein recent IR log spectrum data is weighted more heavily over prior IR log spectrum data.

19. A method for detecting a threat being a threat chemical in illuminated gas samples containing an interferent being an interferent chemical, the threat being in a threat list, interferent and threat being listed in a library of spectra of threats and interferents, the method comprising:

screening, by a gas detector processor, first spectrum data for a first illuminated gas sample to detect a threshold presence of one or more chemicals in the library in the first spectrum data, wherein screening the first spectrum data comprises screening the first spectrum data using a background model to detect the threshold presence of one or more chemicals in the library in the first spectrum data;

holding, by the gas detector processor, the first spectrum data in a buffer, the buffer having a size for storing N spectra, wherein $N \geq 1$, when both (i) no threats on the threat list are detected in the first spectrum data from the screening step and (ii) at least one interferent is detected in the first spectrum data from the screening step; and adding, after the holding step, by the gas processor, the first spectrum data held in the buffer to the background model when screening of the N subsequent spectrum data for the N subsequent illuminated gas samples detects no threats.

20. The method of claim 19, further comprising applying an exponential decay factor to the mean and covariance of the background prior to adding the first spectrum data held in the buffer to the background such that recent spectrum data is weighted heavier than older spectrum data.

\* \* \* \* \*